(12) United States Patent
Schimmels et al.

(10) Patent No.: US 8,721,737 B2
(45) Date of Patent: May 13, 2014

(54) PASSIVE ANKLE PROSTHESIS WITH ENERGY RETURN SIMULATING THAT OF A NATURAL ANKLE

(75) Inventors: Joseph M. Schimmels, Milwaukee, WI (US); Shuguang Huang, Milwaukee, WI (US)

(73) Assignee: Marquette University, Milwaukee, WI (US)

( * ) Notice: Subject to any disclaimer, the term of this patent is extended or adjusted under 35 U.S.C. 154(b) by 233 days.

(21) Appl. No.: 13/365,708

(22) Filed: Feb. 3, 2012

(65) Prior Publication Data

US 2012/0203359 A1 Aug. 9, 2012

Related U.S. Application Data

(60) Provisional application No. 61/439,114, filed on Feb. 3, 2011.

(51) Int. Cl.
*A61F 2/60* (2006.01)

(52) U.S. Cl.
USPC .......................................................... 623/52

(58) Field of Classification Search
USPC .............................................. 623/49–52, 55
See application file for complete search history.

(56) References Cited

U.S. PATENT DOCUMENTS

| | | | |
|---|---|---|---|
| 4,364,128 A * | 12/1982 | Mummert | 623/53 |
| 4,370,761 A | 2/1983 | Serri | |
| 4,442,554 A | 4/1984 | Copes | |
| 4,547,913 A | 10/1985 | Phillips | |
| 4,605,417 A | 8/1986 | Fleischauer | |
| 4,645,509 A | 2/1987 | Poggi et al. | |
| 4,764,172 A | 8/1988 | McCoy | |
| 5,066,305 A | 11/1991 | Firth | |
| 5,156,630 A | 10/1992 | Rappoport et al. | |
| 5,181,932 A | 1/1993 | Phillips | |
| 5,405,411 A | 4/1995 | McCoy | |
| 5,425,780 A | 6/1995 | Flatt et al. | |
| 5,425,781 A | 6/1995 | Allard et al. | |
| 5,486,209 A | 1/1996 | Phillips | |
| 5,509,936 A | 4/1996 | Rappoport et al. | |
| 5,571,212 A | 11/1996 | Cornelius | |
| 5,593,455 A | 1/1997 | Phillips | |
| 5,728,175 A | 3/1998 | Rincoe | |
| 5,913,901 A | 6/1999 | Lacroix | |
| 6,071,313 A | 6/2000 | Phillips | |
| 6,206,934 B1 | 3/2001 | Phillips | |
| 6,280,479 B1 | 8/2001 | Phillips | |
| 6,436,149 B1 | 8/2002 | Rincoe | |
| 6,929,665 B2 | 8/2005 | Christensen | |
| 6,942,704 B2 | 9/2005 | Sulprizio | |
| 7,101,403 B2 | 9/2006 | Chen | |
| 7,578,852 B2 | 8/2009 | Townsend et al. | |
| 7,611,543 B2 | 11/2009 | Townsend et al. | |
| 7,648,533 B2 | 1/2010 | Phillips et al. | |
| 7,819,926 B1 | 10/2010 | Longino | |
| 7,862,622 B2 | 1/2011 | Dunlap et al. | |
| 7,955,399 B2 | 6/2011 | Townsend et al. | |
| 8,480,760 B2 * | 7/2013 | Hansen et al. | 623/52 |
| 2002/0143407 A1 | 10/2002 | Kuiken | |
| 2003/0105531 A1 | 6/2003 | Bunn | |

(Continued)

*Primary Examiner* — Bruce E Snow
(74) *Attorney, Agent, or Firm* — Andrus Intellectual Property Law, LLP

(57) ABSTRACT

Disclosed are passive lower limb prosthetic devices comprising at least a two degree of freedom mechanism and a network of compression springs.

14 Claims, 9 Drawing Sheets

(56) References Cited

U.S. PATENT DOCUMENTS

| | | |
|---|---|---|
| 2004/0064195 A1* | 4/2004 | Herr .................................. 623/24 |
| 2004/0186590 A1 | 9/2004 | Townsend et al. |
| 2004/0225375 A1 | 11/2004 | Chen |
| 2004/0236435 A1 | 11/2004 | Chen |
| 2005/0033450 A1 | 2/2005 | Christensen |
| 2005/0033451 A1 | 2/2005 | Aigner et al. |
| 2005/0038525 A1 | 2/2005 | Doddroe et al. |
| 2005/0049721 A1 | 3/2005 | Sulprizio |
| 2005/0203640 A1 | 9/2005 | Christensen |
| 2005/0267601 A1 | 12/2005 | Chen |
| 2006/0064176 A1 | 3/2006 | Kuiken |
| 2006/0173555 A1* | 8/2006 | Harn et al. ...................... 623/52 |
| 2006/0178754 A1 | 8/2006 | Townsend et al. |
| 2007/0213841 A1 | 9/2007 | Townsend et al. |
| 2007/0219643 A1 | 9/2007 | Townsend et al. |
| 2007/0299544 A1 | 12/2007 | Dunlap et al. |
| 2008/0033579 A1 | 2/2008 | Phillips et al. |
| 2008/0188950 A1 | 8/2008 | Fleury et al. |
| 2008/0228288 A1 | 9/2008 | Nelson et al. |
| 2008/0262635 A1 | 10/2008 | Moser et al. |
| 2008/0281436 A1 | 11/2008 | Townsend et al. |
| 2009/0265018 A1 | 10/2009 | Goldfarb et al. |
| 2009/0281638 A1 | 11/2009 | Tourneux |
| 2009/0319055 A1 | 12/2009 | Iversen et al. |
| 2011/0106274 A1 | 5/2011 | Ragnarsdottir et al. |
| 2011/0257764 A1 | 10/2011 | Herr et al. |

\* cited by examiner

PASSIVE ANKLE PROSTHESIS WITH ENERGY RETURN SIMULATING THAT OF A NATURAL ANKLE

CROSS-REFERENCE TO RELATED APPLICATIONS

This application claims the benefit under 35 U.S.C. §119 (e) to U.S. Provisional Patent Application No. 61/439,114, filed on Feb. 3, 2011, the content of which is incorporated herein by reference in its entirety.

STATEMENT REGARDING FEDERALLY SPONSORED RESEARCH OR DEVELOPMENT

This invention was made with government support under 1R21EB006840-01A2 awarded by the National Institutes of Health. The government has certain rights in the invention.

BACKGROUND

The field of the invention relates to ankle, foot, and lower leg prosthetic devices. In particular, the field of the invention relates to passive ankle, foot, and lower leg prosthetic devices.

Prosthetic ankle and foot devices have been described. (See U.S. Pat. Nos. 7,955,399; 7,862,622; 7,819,926; 7,648,533; 7,611,543; 7,578,852; 7,101,403; 6,942,704; 6,929,665; 6,436,149; 6,280,479; 6,206,934; 6,071,313; 5,913,901; 5,728,175; 5,593,455; 5,571,212; 5,509,936; 5,486,209; 5,425,781; 5,425,780; 5,405,411; 5,181,932; 5,156,630; 5,066,305; 4,764,172; 4,645,509; 4,605,417; 4,547,913; 4,442,554; and 4,370,761; and U.S. Published Patent Application Nos. 20110257764; 20110106274; 20090319055; 20090281638; 20090265018; 20080281436; 20080262635; 20080228288; 20080188950; 20080033579; 20070299544; 20070219643; 20070213841; 20060178754; 20060064176; 20050267601; 20050203640; 20050049721; 20050038525; 20050033451; 20050033450; 20040236435; 20040225375; 20040186590; 20030105531; and 20020143407; the contents of which are incorporated herein by reference in their entireties).

Current commercially available prosthetic ankles/feet are based on passive leaf springs that absorb and release energy during walking. These springs reduce the impact of ground reaction forces that occur during walking and convert some of the absorbed energy into energy used to propel the body forward. The energy stored, however, is significantly less than that required to propel the body forward during push-off. Amputees that use these existing passive devices tend to walk more slowly and expend more energy than normal walkers. To obtain the desired mechanical characteristics, the ankle joint must display active properties. More energy must be extracted from the ankle than was provided in ankle deflection.

Current research in prosthetic ankle design addresses the need for more energy during push-off to propel the body forward. Most current research is directed at bionic ankles in which active components (motors) are used to assist in propelling the body forward. The limitations of these active (or bionic) designs are the increased size and weight of the ankle. The degree to which size and weight increases is roughly determined by the amount of power provided by the actuator to propel the body forward. In order to minimize the increased size and weight, a good prosthesis design is one for which the majority of the desired behavior is obtained using passive elements and only a limited contribution is required of the motors.

The present inventors are unaware of any report in which active behavior using only passive components has been achieved in a prosthetic ankle design. Typically, prior passive designs do not simulate natural ankle mechanical characteristics. Furthermore, prior active designs require large, heavy actuators to achieve similar mechanical characteristics. The presently disclosed devices do not need sensors or actuators to achieve the active behavior associated with normal walking.

SUMMARY

Disclosed are lower limb prosthetic devices comprising at least a two degree of freedom mechanism and a network of conventional springs. One degree of freedom allows a lower leg component to compress slightly when the weight of the amputee is applied during walking. The second degree of freedom allows rotation about the prosthetic ankle joint. The force generated along the leg during walking is converted into ankle torque used to propel the body forward during push-off. As a result, more energy is released by the ankle than has been stored in ankle deflection. In this way active behavior during push-off is achieved with purely passive elements. Because of this, the need for a relatively large and heavy motor to generate the torque for push-off is eliminated. This lightweight ankle prosthesis will allow an amputee to walk with a near-normal gait.

In the disclosed devices, the energy stored along one degree of freedom (generated by the weight of the amputee) is released along a different degree of freedom to achieve mechanical characteristics very similar to a natural ankle. As such, the ankle is capable of demonstrating "active behavior". More energy is released at the ankle joint than that stored in ankle deflection. The energy stored in leg deflection is added to the energy stored in ankle deflection. This total energy is then released during push-off.

The prosthetic devices typically comprise: (a) a top body for attaching to a residual leg limb of an amputee; (b) a middle body movably attached to the top body; and (c) a foot body movably attached to the top body and the middle body. The top body and the middle body may be movably attached via a bracket and a substantially vertical spring mechanism biasing the top body away from the middle body, namely SM 1. The foot body may be movably attached to the top body and the middle body via the bracket, where the foot body is rotatably attached to the bracket at an ankle joint. The foot body further may be movably attached to the bracket via: (i) a substantially horizontal or diagonal spring mechanism, namely SM2, rotatably attached to the foot body via a back axle and rotatably attached to the bracket via a center axle, the SM2 biasing the foot body away from the bracket; (ii) a substantially vertical spring mechanism, namely SM3, rotatably attached to the foot body via a bottom axle and rotatably attached to the bracket via a top movable axle, the SM3 biasing the foot body away from the bracket; and (iii) a substantially diagonal spring mechanism, namely SM4, rotatably attached to the foot body via a front axle and rotatably attached to the bracket via the center axle, the substantially diagonal spring mechanism biasing the foot body away from the bracket.

The bracket typically includes a curved slot that that curves downward and forward, the top movable axle being positioned in the curved slot and being movable from a top position of the curved slot to a bottom position of the curved slot via substantially downward vertical movement of the top body. The device also may include a catch mechanism and a release mechanism for catching and releasing the top movable axle. The catch mechanism may be attached to the bracket and may catch and hold the top movable axle in the bottom position of the curved slot. The release mechanism may be rotatably attached to the bracket and may move the catch mechanism via substantially upward vertical movement of the top body thereby releasing the top movable axle and permitting the top movable axle to move from the bottom position of the curved slot to the top position of the curved slot.

DETAILED DESCRIPTION

The subject matter disclosed herein is described using several definitions, as set forth below and throughout the application.

As used herein, the terms "include" and "including" have the same meaning as the terms "comprise" and "comprising."

As used herein, "substantially horizontal" means positioned at an angle of no more than about positive or negative 20 degrees, preferably at an angle of no more than about positive or negative 10 degrees, preferably no at an angle of no more than about positive or negative 5 degrees. As used herein, "substantially vertical" means positioned at an angle of about 70 degrees to about 110 degrees, preferably at an angle of about 80 degrees to about 100 degrees, more preferably at an angle of about 85 degrees to an angle of about 95 degrees. As used herein, "substantially diagonal" means positioned at an angle of about 20 degrees to about 70 degrees, preferably at an angle of about 30 degrees to about 60 degrees, more preferably at an angle of about 35 degrees to about 55 degrees, even more preferably at an angle of about 40 degrees to about 50 degrees.

Figure 1:
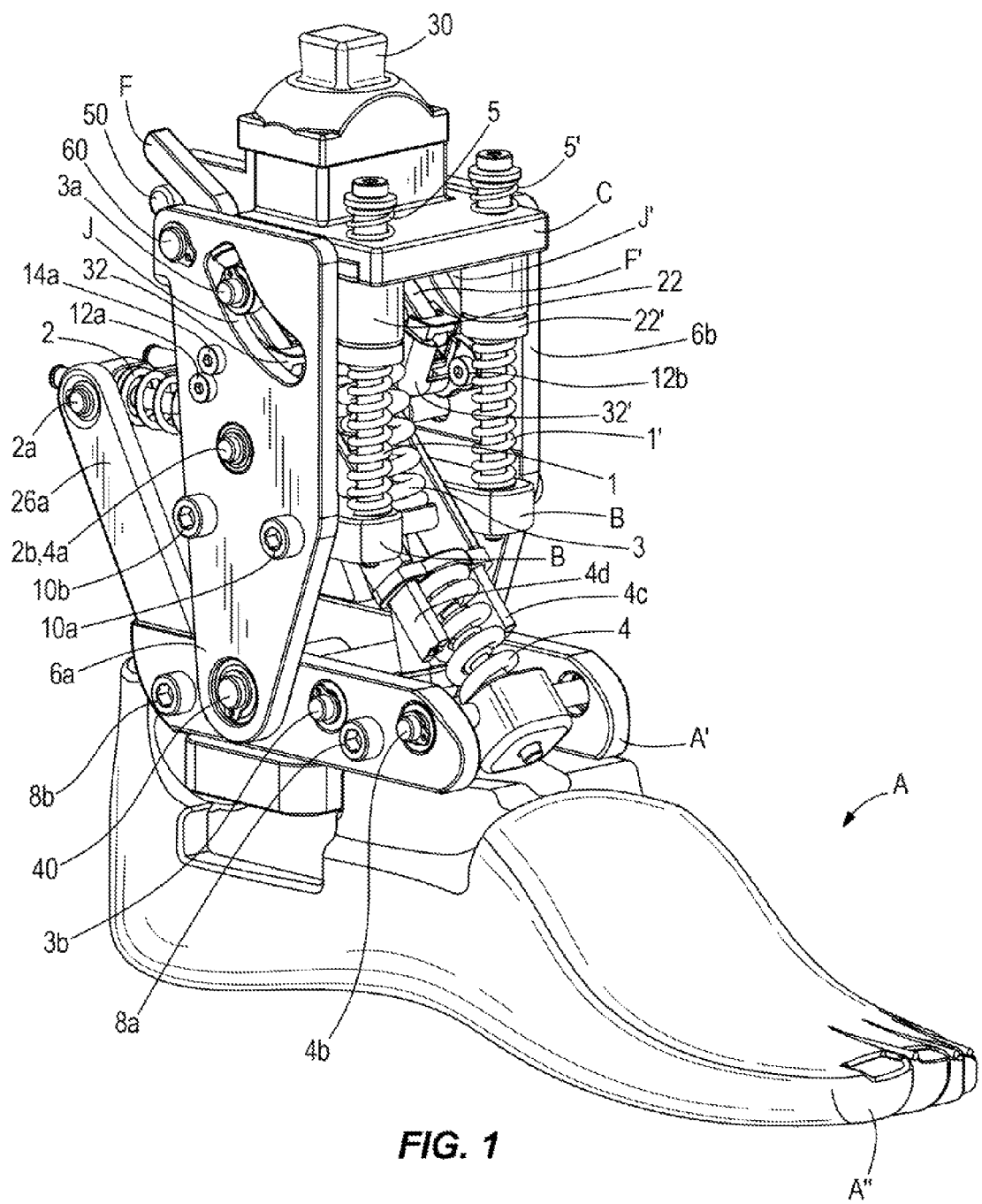
FIG. 1 illustrates one embodiment of a prosthetic device as disclosed herein from a front perspective view.
Figure 2:
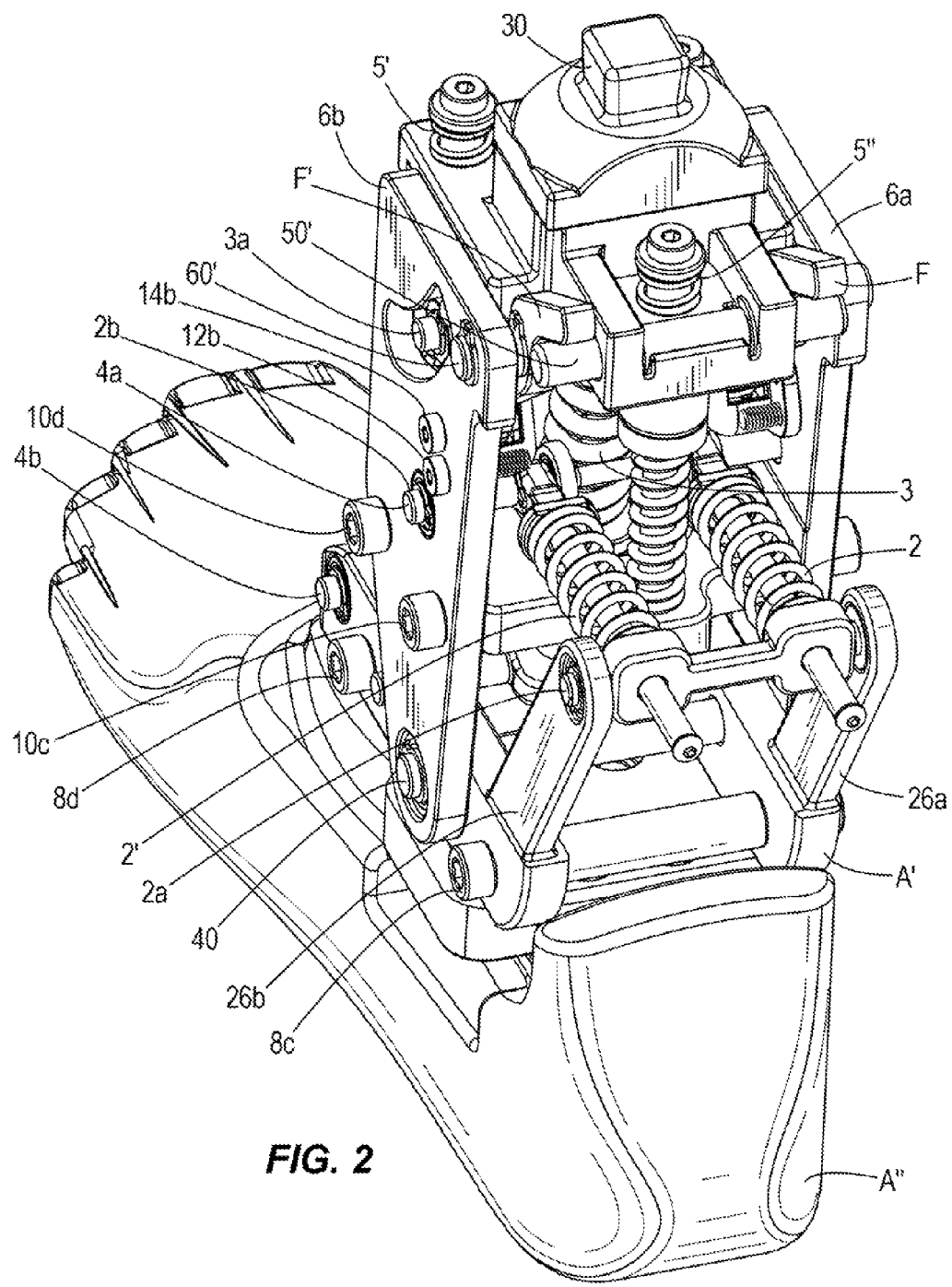
FIG. 2 illustrates one embodiment of a prosthetic device as disclosed herein from a back perspective view.

Referring now to the figures, FIGS. 1 and 2 illustrate one embodiment of a prosthetic device as disclosed herein. The device has a foot body A, a middle body B, and a top body C for attaching to a residual lower limb of an amputee. The foot body has an attaching plate A' and a replaceable foot portion A", preferably comprising resilient material. The attaching plate A' is attached to the foot body A" via bolting mechanisms 8a,8b,8c,8d. The top body C and middle body B are movably attached via a bracket 6a,6b and substantially vertical spring mechanism 1 (or SM1) comprising one or more spring and a shaft and biasing the top body C and the middle body B away from each other. Shown is an optional second mechanism 1' and a third mechanism 1". Also shown are optional upper cushion spring mechanisms 5,5' and linear bearings 22,22' to reduce friction. The top body may include an anchor body 30 for anchoring to the residual lower limb of the amputee. The device also includes a bracket comprising bracket arms 6a, 6b. The top body C and the middle body B are movably attached via the bracket 6a,6b. Middle body B is attached to the bracket 6a,6b by bolting mechanism 10a,10b, 10c,10d.

The foot body A is movably attached to the top body C and the middle body B at the attaching plate A' via the bracket 6a,6b. The attaching plate A' and the bracket 6a,6b are rotatably attached at an ankle joint 40. The foot body A further is movably attached at the attaching plate A' to the bracket 6a,6b via: (i) a substantially horizontal spring mechanism 2 (or SM2) and optional second substantially horizontal spring mechanism 2' (which alternatively may be substantially diagonal spring mechanisms), rotatably attached to the foot body A via a back axle 2a and rotatably attached to the bracket 6a,6b via a center axle 2b,4a, where 2,2' biases the foot body A away from the bracket 6a,6b; (ii) a substantially vertical spring mechanism 3 (or SM3) rotatably attached to the foot body A via a bottom axle 3b and rotatably attached to the bracket 6a,6b via a top movable axle 3a, where 3 biases the foot body A away from the bracket 6a,6b; and (iii) a substantially diagonal spring mechanism 4 (or SM4) rotatably attached to the foot body A via a front axle 4b and rotatably attached to the bracket via the center axle 2b,4a, where 4 biases the foot body A away from the bracket 6a,6b. Back axle 2a of spring mechanism 2 is supported by wing arms 26a,26b. Spring mechanism 4 includes parallel support arms 4c,4d through which spring mechanism 3 passes.

As shown in FIGS. 1 and 2, the bracket 6a,6b has a curved slot J,J' having a downward and forward curve shape. The top movable axle 3a of spring mechanism 3 is positioned in the curved slot J,J' and is movable therein from a top position to a bottom position of the curved slot J,J' via movement of top body C.

Figure 3:
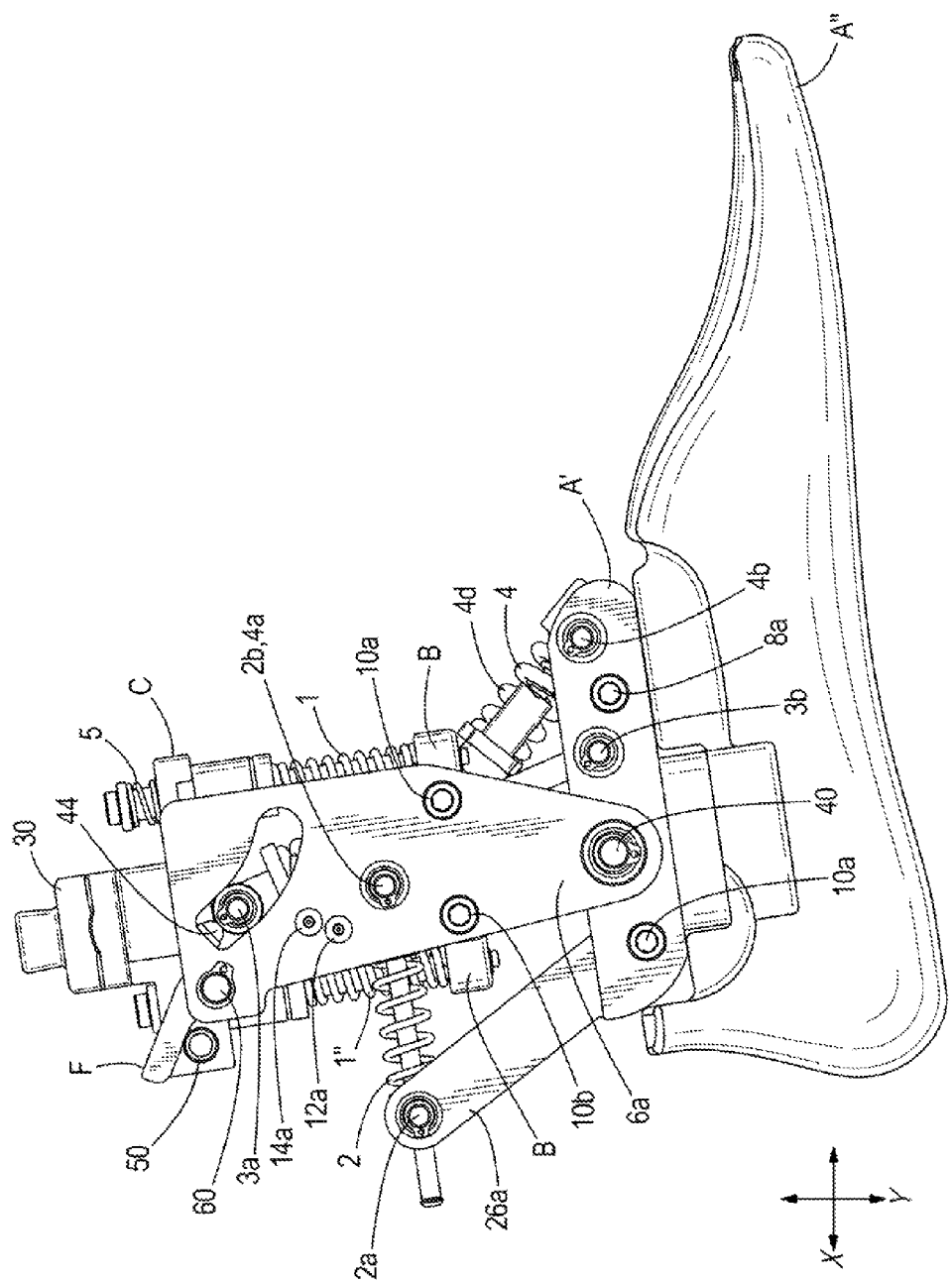
FIG. 3 illustrates one embodiment of a prosthetic device at an unloaded/swing position from a side view.
Figure 4:
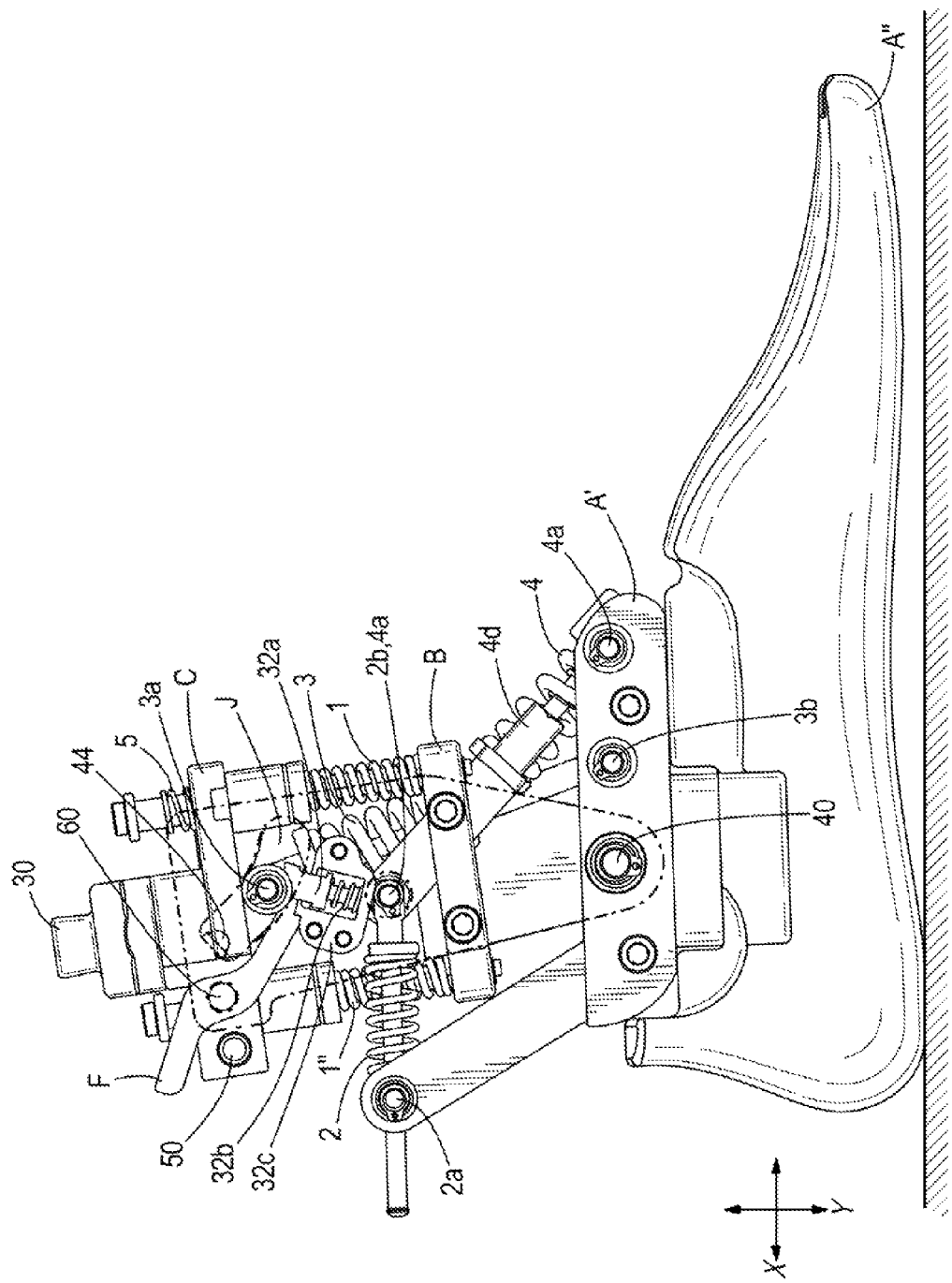
FIG. 4 illustrates one embodiment of a prosthetic device at heel-strike position from a side view.

As shown in FIG. 3, prior to the device contacting the ground, the springs and bodies of the device are in their unloaded positions. FIG. 4 illustrates one embodiment of a prosthetic device at heel-strike position. At heel-strike, the heel of the foot body A contacts the ground, which causes spring mechanism 2 to compress generating torque about the pin joint 40 on the foot. Spring mechanisms 1 and 3 begin to compress under the weight of the amputee via the top body C moving substantially vertically downward towards middle body B and foot body A.

Figure 5:
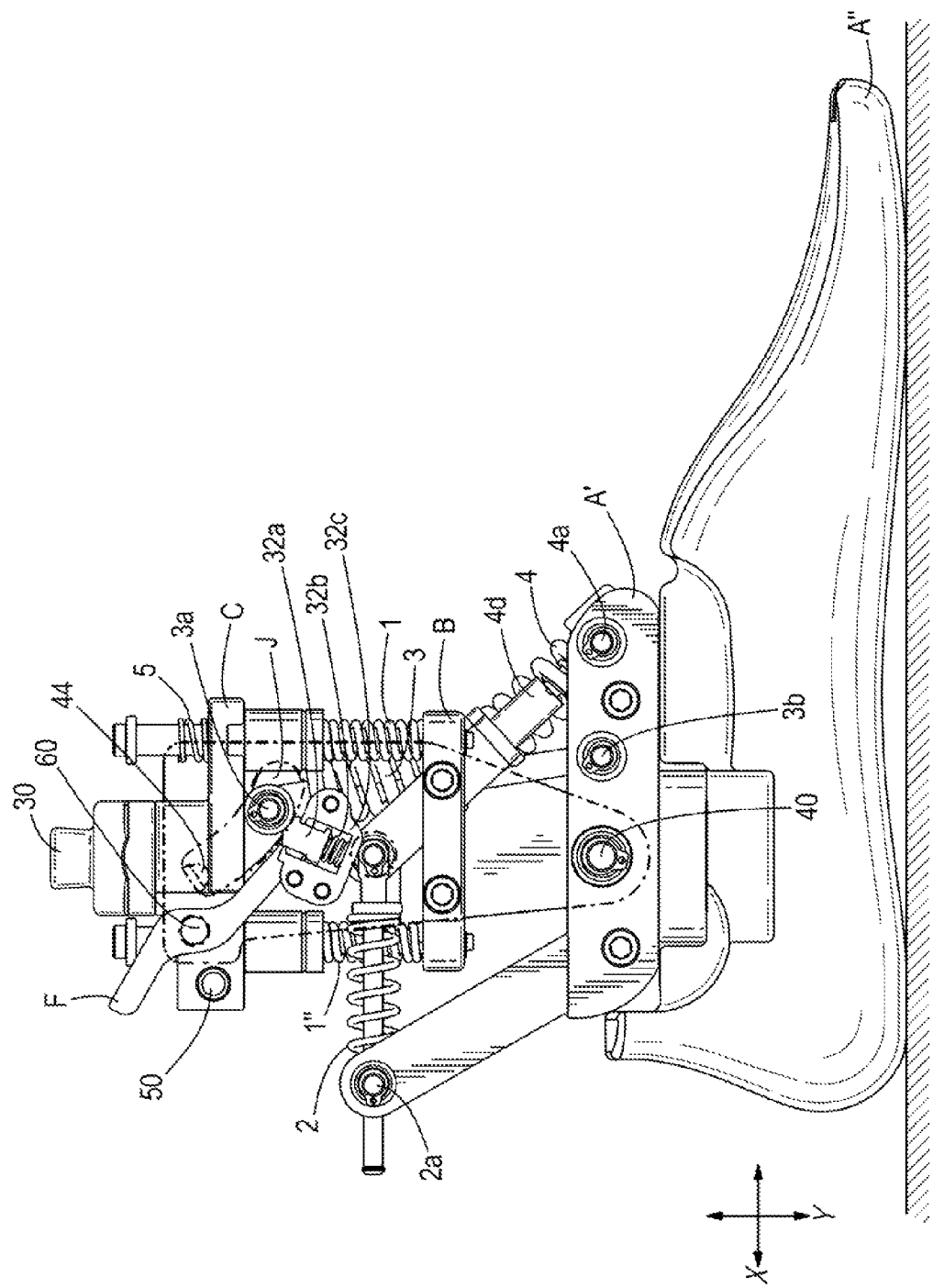
FIG. 5 illustrates one embodiment of a prosthetic device at a lightly loaded foot-flat position from a side view.

FIG. 5 illustrates one embodiment of a prosthetic device at a lightly loaded foot-flat position. As walking continues, spring mechanism 2 returns to its free-length and spring mechanisms I and 3 continue to compress via substantially vertically downward movement of top body C towards middle body B and foot body A.

Figure 6:
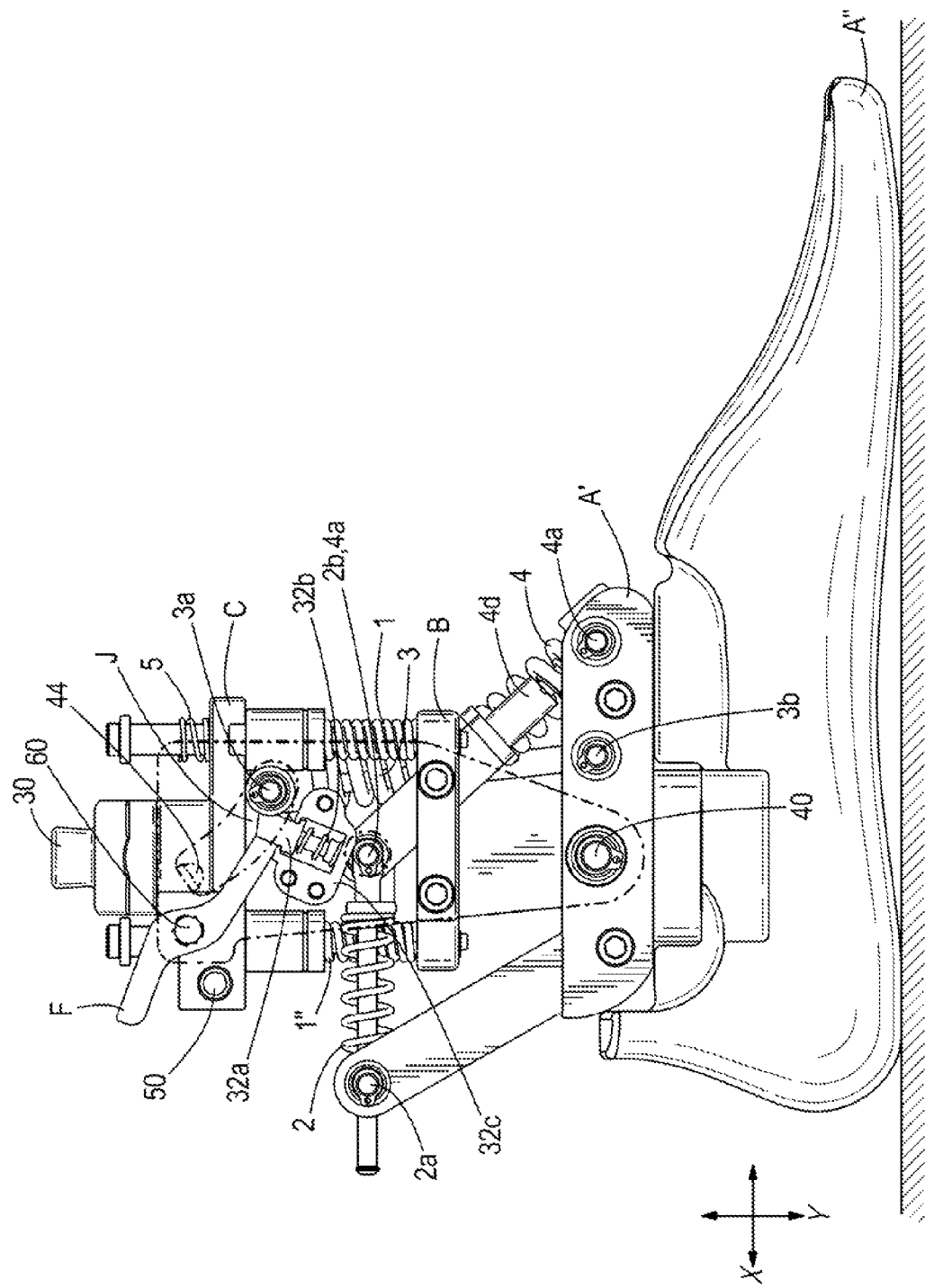
FIG. 6 illustrates one embodiment of a prosthetic device at a fully loaded foot-flat position from a side view.

FIG. 6 illustrates one embodiment of a prosthetic device at fully loaded foot-flat. When fully loaded with the amputee's weight, spring mechanisms I and 3 are fully compressed via substantially vertically downward movement of top body C towards middle body B and foot body A. As top body C moves substantially vertically downward, top movable axle 3a moves along the curved slot J in the bracket 6a,6b and, in doing so, increases the torque about the ankle joint 40. This converts the deflection of spring mechanism 3 caused by the weight load to increased torque about the ankle.

Figure 7:
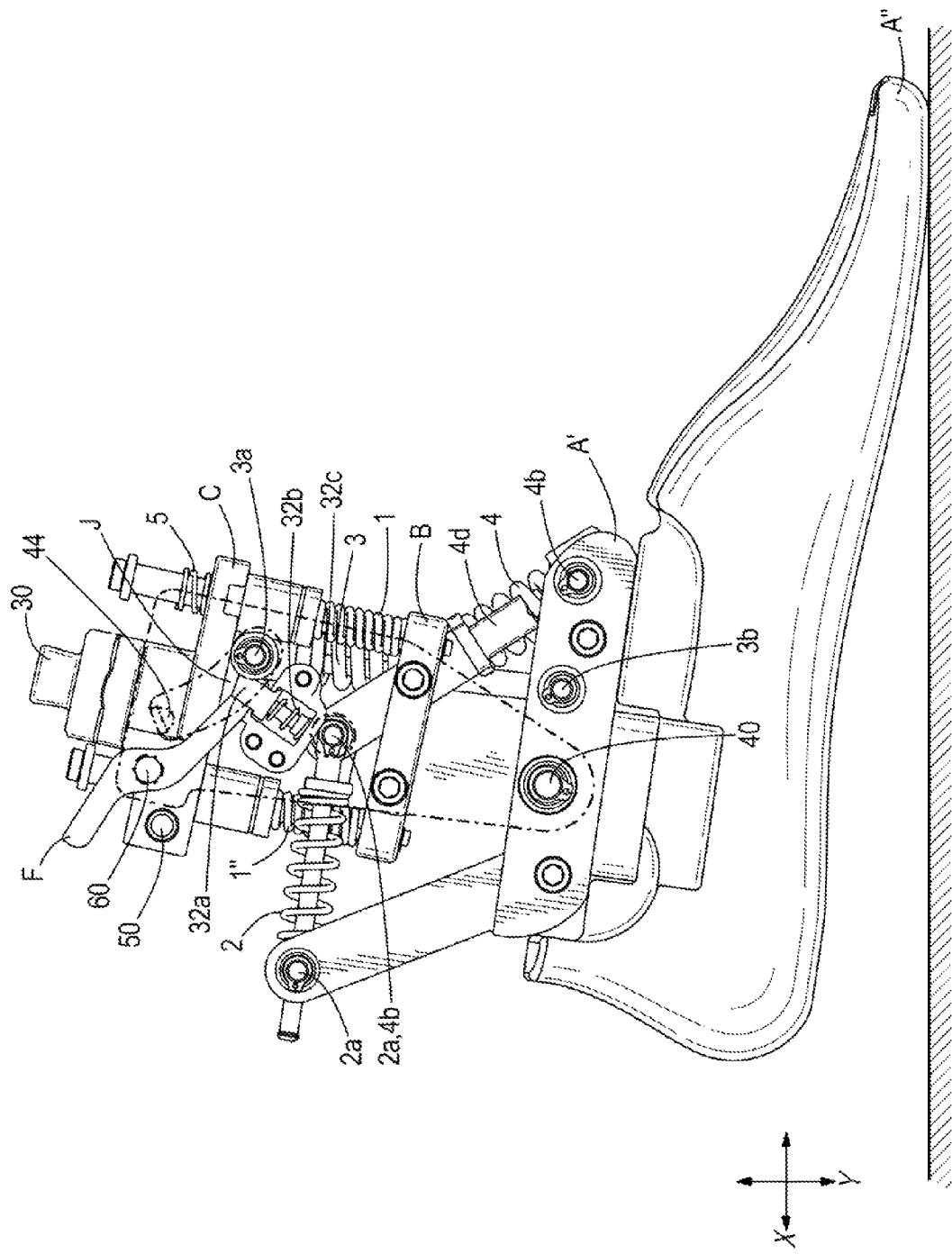
FIG. 7 illustrates one embodiment of a prosthetic device at a charged/locked position from a side view.

FIG. 7 illustrates one embodiment of a prosthetic device at a charged/locked position. The energy stored in spring mechanism 3 is not returned immediately to move top body C back to its original position. Instead, this energy is used to propel the body forward during push-off. A catch mechanism 32a;32b,32c is used to block the return of spring mechanism 3 back to its free length position by catching and holding the top movable axle 3a of spring mechanism 3. Spring mechanism 3 generates sufficient torque about the ankle joint 40 to push the foot body A down and propel the body forward. As shown, catch mechanism includes an angled tooth 32a, a catch spring 32b biasing the angled tooth 32a in a closed position, and a catch housing 32c. The catch mechanism is attached to the bracket 6a,6b via bolting mechanisms 12a, 12b,14a,14b. As the top movable axle 3a of spring mechanism 3 moves from the top position of the curved slot J,J' to the bottom position of the curved slot J,J', the top movable axle 3a moves over the angled tooth 32a pushing the angled tooth downward to an open position. The angled tooth 32a moves back to the closed position after the top movable axle moves past the angled tooth via the biasing spring catch 32b.

Figure 8:
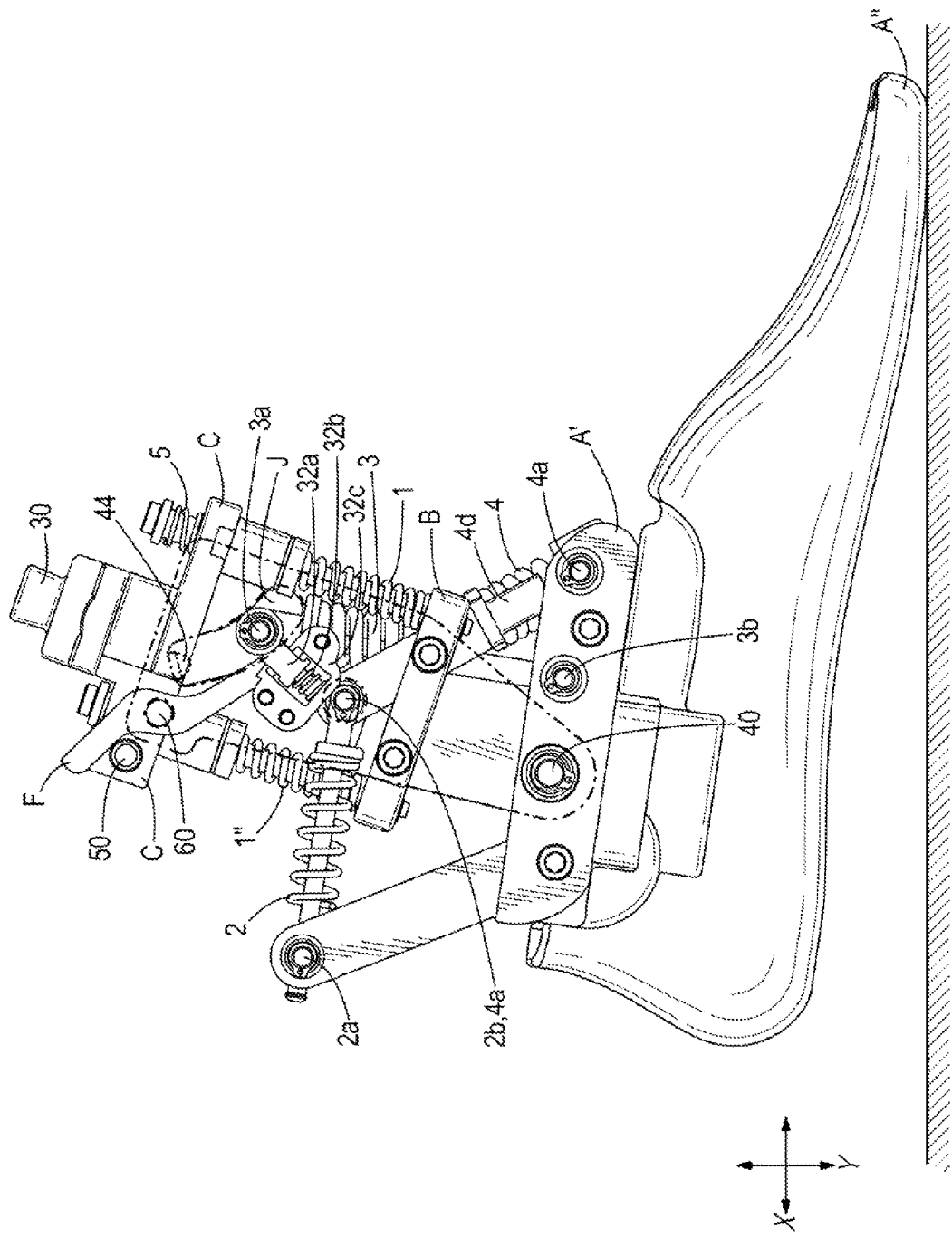
FIG. 8 illustrates one embodiment of a prosthetic device at a trigger/release position from a side view.

FIG. 8 illustrates one embodiment of a prosthetic device at a trigger/release position. As the amputee begins to lift his leg, top body C moves up relative to middle body B. A release mechanism F,F' is rotatably attached to middle body B via an axle 60. Pin 50 on the top body C contacts the release mechanism F,F' and causes the release mechanism F,F' to rotate about pin joint 60 and push angled tooth 32a down and out of the way of top movable axle 32a so that the top movable axle 3a of spring mechanism 3 is free to move to the top position of the curved slot J,J' further to its bias and the ankle can return to its original unloaded state.

Figure 9:
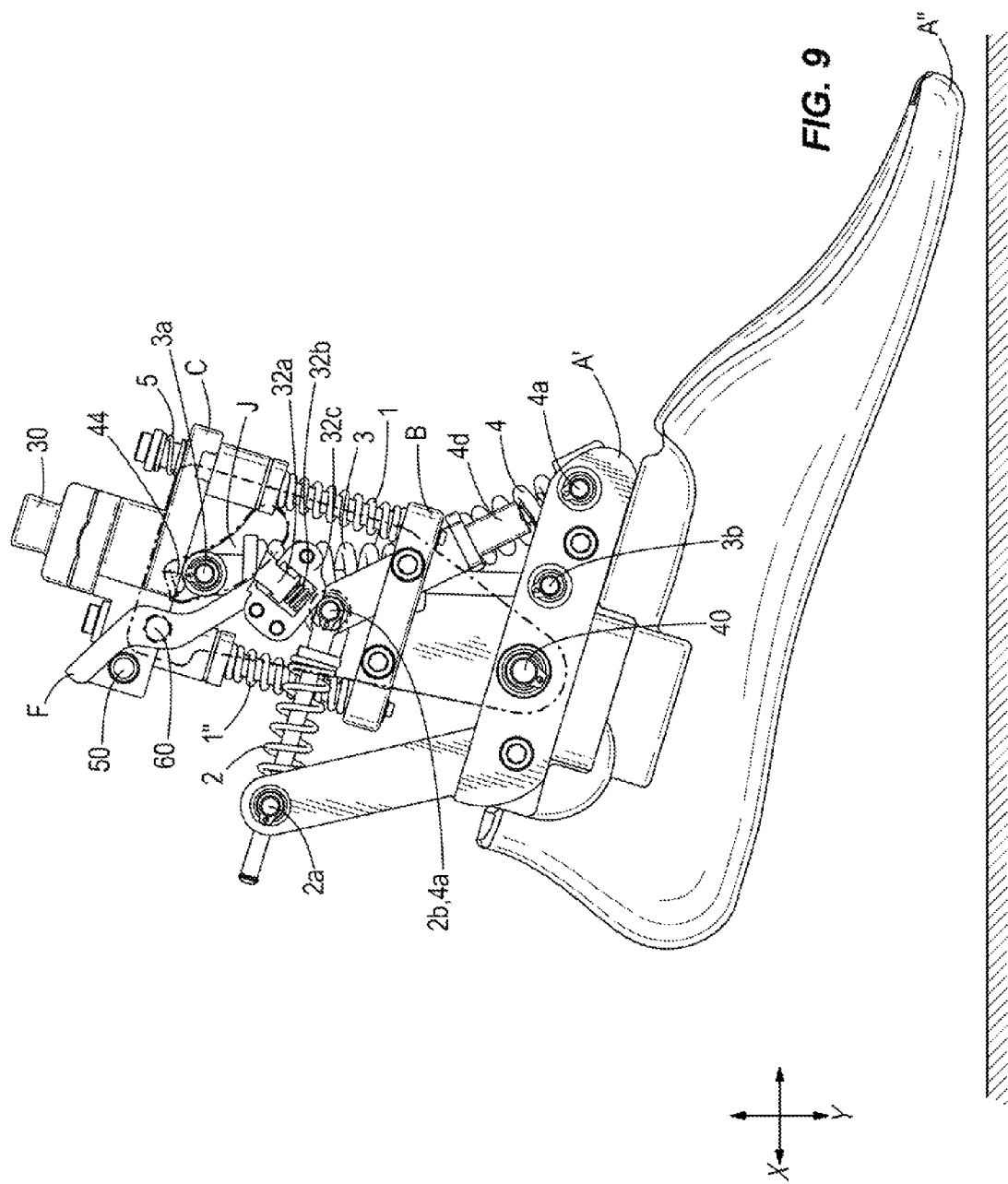
FIG. 9 illustrates one embodiment of a prosthetic device at an unloaded/swing position from a side view.

FIG. 9 illustrates one embodiment of a prosthetic device at an unloaded/swing position. Once the leg is fully lifted by the amputee, the bodies and springs return to their unloaded positions. Bumper 44 (preferably comprising resilient material) cushions the return of the top movable axle 32a to the top position of curved slot J,J'. Optional upper cushion spring mechanisms 5,5' cushion the return of top body C to its unloaded position.

It will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

What is claimed is:
1. A prosthetic device comprising:
(a) a top body for attaching to a residual leg limb of an amputee;
(b) a middle body movably attached to the top body via a bracket and via a substantially vertical spring mechanism biasing the top body away from the middle body, namely SM1;
(c) a foot body movably attached to the top body and the middle body via:
(i) the bracket, the foot body rotatably attached to the bracket at an ankle joint;
(ii) a substantially horizontal or diagonal spring mechanism, namely SM2, rotatably attached to the foot body via a back axle and rotatably attached to the bracket via a center axle, the SM2 biasing the foot body away from the bracket;
(iii) a substantially vertical spring mechanism, namely SM3, rotatably attached to the foot body via a bottom axle and rotatably attached to the bracket via a top movable axle, the SM3 biasing the foot body away from the bracket, wherein the bracket comprises a curved slot that curves downward and forward, the top movable axle being positioned in the curved slot and being movable from a top position of the curved slot to a bottom position of the curved slot via substantially downward vertical movement of the top body;
(iv) a substantially diagonal spring mechanism, namely SM4, rotatably attached to the foot body via a front axle and rotatably attached to the bracket via the center axle, the substantially diagonal spring mechanism biasing the foot body away from the bracket;
(d) a catch mechanism attached to the bracket that catches and holds the top movable axle in the bottom position of the curved slot; and
(e) a release mechanism rotatably connected to the bracket via a top axle, wherein the release mechanism moves the catch mechanism via substantially upward vertical movement of the top body thereby permitting the top movable axle to move from the bottom position of the curved slot to the top position of the curved slot.

2. The device of claim 1, wherein as the amputee contacts ground with the device, SM1 and SM3 are compressed by weight of the amputee, and SM2 is compressed and generates torque at the ankle joint.

3. The device of claim 2, wherein as the amputee moves forward after having contacted ground with the device, SM2 returns to its uncompressed length and SM1 and SM3 are further compressed.

4. The device of claim 3, wherein when the device is fully loaded with weight of the amputee, the top body moves the top movable axle of SM3 along the curved slot from the top position to the bottom position and increases torque at the ankle joint.

5. The device of claim 4, wherein after the top movable axle of SM3 moves from the top position of the curved slot to the bottom position of the curved slot, the top movable axle is caught by the catch mechanism.

6. The device of claim 5, wherein the catch mechanism comprises an angled tooth biased in a closed position via a catch spring contained in a catch housing.

7. The device of claim 6, wherein as the top movable axle of SM3 moves from the top position of the curved slot to the bottom position of the curved slot, the top movable axle moves over the angled tooth pushing the angled tooth downward to an open position, the angled tooth moving back to the closed position after the top movable axle moves past the angled tooth.

8. The device of claim 7, wherein the top body comprises a pin that contacts the release mechanism causing the release mechanism to rotate and move the catch mechanism as the top body moves upward from the middle body.

9. The device of claim 5, wherein the increased torque at the pin joint is sufficient to push the foot body down and propel the amputee forward.

10. The device of claim 9, wherein as the amputee begins to move forward, the bracket rotates forward at the ankle joint and SM4 is compressed.

11. The device of claim 9, wherein as the amputee begins to move forward and lift the device, the top body moves upward from the middle body and the release mechanism contacts and moves the catch mechanism thereby releasing the top movable axle.

12. The device of claim 1, wherein the foot body comprises an attachment plate and the foot body is attached to the bracket at the ankle joint via the attachment plate.

13. The device of claim 12, wherein the foot body further comprises a replaceable foot portion.

14. The device of claim 13, wherein the replaceable foot portion comprises resilient material.

* * * * *